(12) United States Patent
Yamazaki

(10) Patent No.: US 8,773,522 B2
(45) Date of Patent: Jul. 8, 2014

(54) ENDOSCOPE APPARATUS

(75) Inventor: Kenji Yamazaki, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1051 days.

(21) Appl. No.: 12/362,952

(22) Filed: Jan. 30, 2009

(65) Prior Publication Data

US 2009/0141125 A1 Jun. 4, 2009

Related U.S. Application Data

(63) Continuation of application No. PCT/JP2007/058670, filed on Apr. 20, 2007.

(30) Foreign Application Priority Data

Aug. 3, 2006 (JP) ................... 2006-212561

(51) Int. Cl.
*A61B 1/06* (2006.01)
*A62B 1/04* (2006.01)
*H04N 7/18* (2006.01)
*A61B 1/00* (2006.01)

(52) U.S. Cl.
CPC ............. *A61B 1/0638* (2013.01); *A61B 1/0646* (2013.01); *A61B 1/00186* (2013.01)
USPC ..................... 348/70; 348/61; 348/65; 348/68

(58) Field of Classification Search
CPC . A61B 1/0638; A61B 1/0646; A61B 1/00186
USPC .......................................................... 348/70
See application file for complete search history.

(56) References Cited

U.S. PATENT DOCUMENTS 4,878,113 A 10/1989 Nakamura
4,885,634 A 12/1989 Yabe
(Continued)

FOREIGN PATENT DOCUMENTS

EP 1 302 152 A1 4/2003
EP 1 531 629 A1 5/2005
(Continued)

OTHER PUBLICATIONS

Extended Supplementary European Search Report dated Feb. 12, 2010.

*Primary Examiner* — Joseph Greene
(74) *Attorney, Agent, or Firm* — Scully, Scott, Murphy & Presser, P.C.

(57) ABSTRACT

A band-limiting filter of the invention exhibits a trimodal filter characteristic, and includes, for example, band-limiting transmittance filter characteristic portions Rb, Gb, and Bb for wavelength regions of red, green, and blue, respectively. More specifically, the band-limiting transmittance filter characteristic portions Rb, Gb, and Bb, for example, have band-pass characteristics in which the respective center wavelengths are 630 nm (full width at half maximum λ1=30 to 90 nm), 540 nm (full width at half maximum λ2=20 to 60 nm), and 440 nm (full width at half maximum λ3=50 to 80 nm). This makes it possible to obtain an image of a predetermined color tone by restraining an influence of spectral sensitivity characteristic of an image pickup device when the band-limiting filter is applied to a synchronous type endoscope for performing color image pickup to perform observation under normal illumination light.

6 Claims, 13 Drawing Sheets

(56) References Cited

U.S. PATENT DOCUMENTS

| | | | |
|---|---|---|---|
| 5,187,572 A | 2/1993 | Nakamura et al. | |
| RE34,411 E * | 10/1993 | Nishioka et al. | 348/70 |
| 5,833,339 A * | 11/1998 | Sarayeddine | 353/20 |
| 7,479,990 B2 * | 1/2009 | Imaizumi et al. | 348/223.1 |
| 2009/0027489 A1 * | 1/2009 | Takemura | 348/65 |

FOREIGN PATENT DOCUMENTS

| | | |
|---|---|---|
| EP | 1 787 577 A1 | 5/2007 |
| JP | 01-308528 | 12/1989 |
| JP | 2002-095635 | 4/2002 |
| JP | 2006-061620 | 3/2006 |
| JP | 2006-141711 | 6/2006 |
| WO | WO2006/025334 A1 | 3/2006 |

* cited by examiner

SPECTRAL PRODUCT OF: SPECTRAL SENSITIVITY X2 (λ) OF SECOND CCD; AND SPECTRAL PRODUCT Ec(λ) OF CONVENTIONAL SYSTEM : X= R, G, B

SPECTRAL PRODUCT OF: SPECTRAL SENSITIVITY B1 (λ) OF B SIGNAL OF FIRST CCD; AND SPECTRAL PRODUCT Ec(λ) OF CONVENTIONAL SYSTEM

SPECTRAL SENSITIVITY CHARACTERISTIC OF COMPLEMENTARY COLOR FILTER

ENDOSCOPE APPARATUS

CROSS REFERENCE TO RELATED APPLICATION

This application is a continuation application of PCT/JP2007/058670 filed on Apr. 20, 2007 and claims benefit of Japanese Application No. 2006-212561 filed in Japan on Aug. 3, 2006, the entire contents of which are incorporated herein by this reference.

BACKGROUND OF INVENTION

1. Field of the Invention

The present invention relates to an endoscope apparatus, and particularly to a synchronous type endoscope apparatus for performing color image pickup.

2. Description of the Related Art

In recent years, electronic endoscopes including image pickup means have been widely employed in various endoscopic inspections and the like.

Electronic endoscope apparatuses used when performing endoscopic inspection include a synchronous type endoscope apparatus which performs color image pickup under white light as illumination light using an image pickup device provided with a color optical filter, and a frame-sequential type endoscope apparatus which performs image pickup respectively under frame-sequential RGB lights as illumination lights by using a monochrome image pickup device and generates a color image. The apparatuses have different image processing systems.

In addition, Japanese Patent Application Laid-Open Publication No. 2002-95635, for example, discloses an endoscope apparatus capable of displaying a running state of blood vessels in the vicinity of a mucosa surface layer with respect to the depth direction, which tends to be buried in optical information obtained under a normal visible light, as more easily identifiable image information by using a narrow-band illumination light.

In a synchronous type endoscope apparatus which performs color image pickup, a complementary color filter as shown in FIG. 18, for example, as a color separation filter 30 for optically separating colors, is mounted on an image pickup surface of a CCD as an image pickup device, on a pixel basis.

The complementary color filter has color chips in four colors, magenta (Mg), green (G), cyan (Cy) and yellow (Ye) which are arranged in front of the respective pixels with Mg and G being alternately arranged in the horizontal direction, and the arrays Mg, Cy, Mg, Ye and G, Ye, G, Cy being arranged in that order in the vertical direction.

In the CCD using the complementary color filter, two columns of pixels adjacent to each other in the vertical direction are added and sequentially read out such that the columns of pixels are shifted with respect to each other in odd fields and even fields. A luminance signal Y and color difference signals Cr, Cb are then generated, as is known, by the color separation circuit in a subsequent stage.

Specifically, when reading out the pixels in n-line, readout signals are "Mg+Cy", "G+Ye", . . . and when reading out the pixels in n−1 line, the read signals are "Mg+Ye", "G+Cy", FIG. 19 shows an example of spectral sensitivity characteristics of these readout signals "Mg+Cy", "G+Ye", "Mg+Ye" and "G+Cy".

Then, the luminance signal Y and the color difference signals Cr, Cb having the spectral characteristics as shown in FIG. 20 are generated by the color separation circuit in the subsequent stage, and the signals passes a known matrix circuit to be converted into RGB signals.

However, the spectral sensitivity characteristics of each of the CCDs having the complementary color filter sometimes differ from each other. FIG. 21 shows the spectral sensitivity characteristics of readout signals of a CCD (for example, a second CCD) which is different from the one shown in FIG. 19.

When the spectral sensitivity characteristics of the readout signals thus differ, the spectral sensitivity characteristic of the RGB signals obtained through the matrix circuit also differs from the first CCD to the second CCD, for example, as shown in FIGS. 23, 24.

Actual image signal intensity reflected on the image is obtained based on the spectral sensitivity characteristics of the respective RGB signals. That is, when the intensity of a signal X (X is one of R, G, and B) of a pixel (i, j) is assumed to be X(i, j), the actual image signal intensity can be obtained by using the following expression.

[Expression 1]

$$X(i,j)=\int E(\lambda)\cdot Sx(\lambda)\cdot O(i,j,\lambda)d\lambda \tag{1}$$

Here, E(λ) represents a comprehensive spectral product obtained by multiplying the spectral radiance of the light source, the spectral transmission factors of the infrared cut filter and the condensing lens, the spectral transmission factor of the light guide of the endoscope, the spectral transmission factors of the illumination lens and the objective lens provided in front of the CCD, and the like. Sx(λ) represents the spectral sensitivity of the signal X (X is one of the R, G, and B) calculated through the matrix circuit based on the spectral sensitivity of the CCD. O (i, j, λ) represents the spectral reflectance of the subject.

Therefore, even if the spectral product E(λ) and the spectral reflectance of the subject O(i, j, λ) are the same, when the spectral sensitivities Sx(λ) of the RGB signals change due to the difference in the spectral sensitivities of the CCDs mounted to the endoscope, the intensity balance of the RGB signals changes when observing a living mucosa whose spectral reflectance complexly changes in integral wavelength ranges though white balance processing is performed in a white balance circuit. As a result, image quality differs in the reproduced color tone from one endoscope to another.

SUMMARY OF THE INVENTION

An endoscope apparatus according to one aspect of the present invention is an endoscope apparatus for performing signal processing to generate a video signal based on a signal outputted from an image pickup section which is mounted to an endoscope and includes a color separation optical filter to perform color image pickup, and the endoscope apparatus includes a band-limited normal illumination light generation section for generating a discrete band-limited normal illumination light by limiting light in visible light range of RGB to within a bandwidth with a predetermined light amount in a normal observation mode.

DETAILED DESCRIPTION OF THE PREFERRED EMBODIMENT(S)

Hereinafter, an embodiment of the present invention will be described with reference to the drawings.

Embodiment 1

Figure 1:
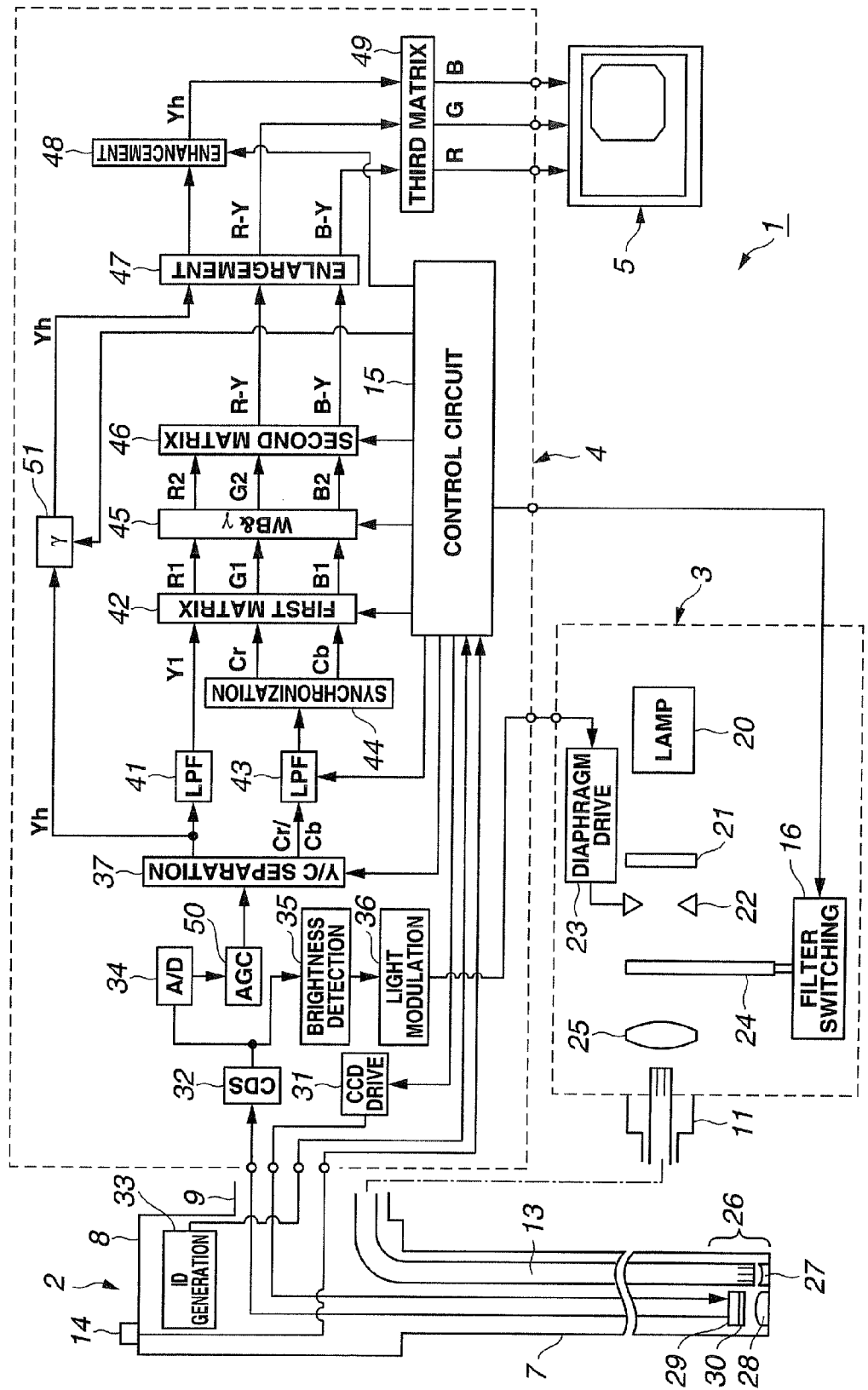
FIG. 1 is a configuration diagram showing a configuration of an endoscope apparatus according to embodiment 1 of the present invention.
Figure 2:
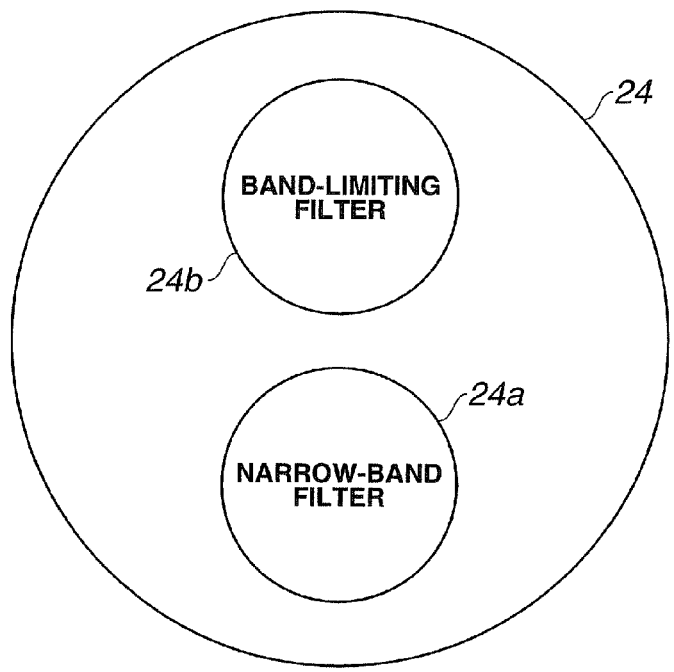
FIG. 2 is a view showing a configuration of a filter in FIG. 1.
Figure 3:
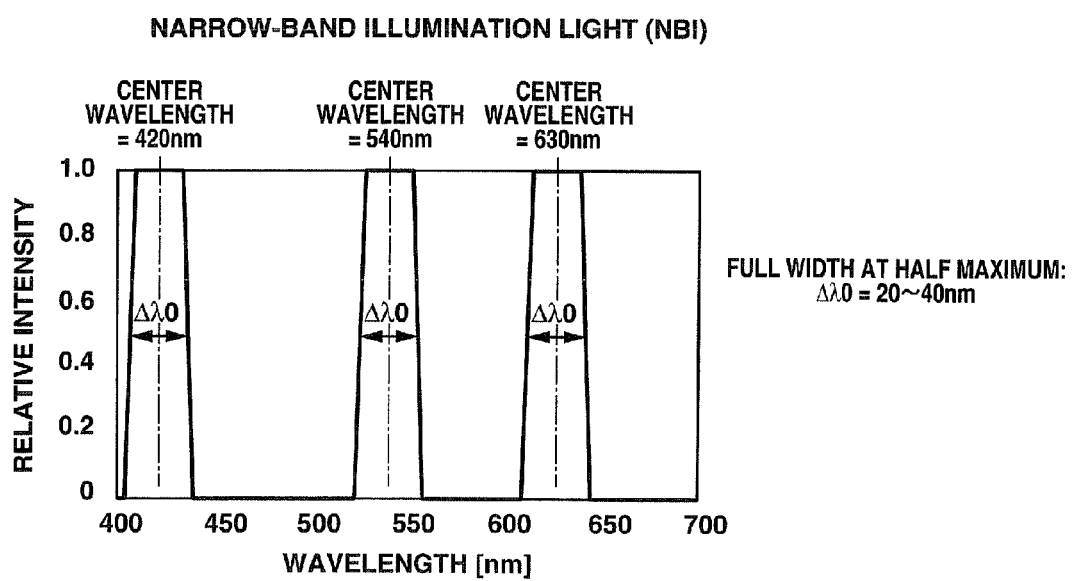
FIG. 3 is a view showing one example of spectral characteristics of RGB lights exhibited by a narrow-band filter in FIG. 2.
Figure 4:
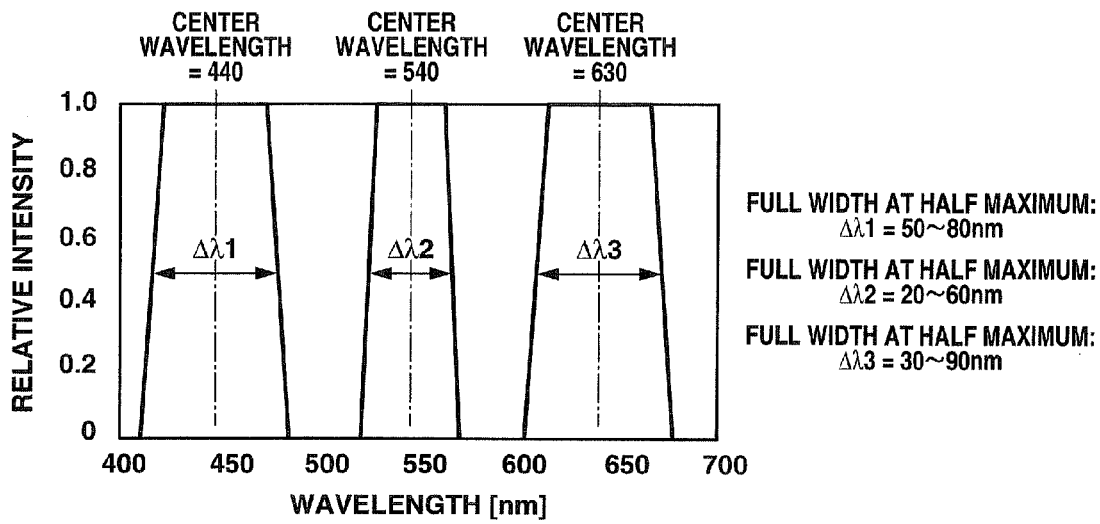
FIG. 4 is a view showing one example of spectral characteristics of RGB lights exhibited by a band-limiting filter in FIG. 2.
Figure 5:
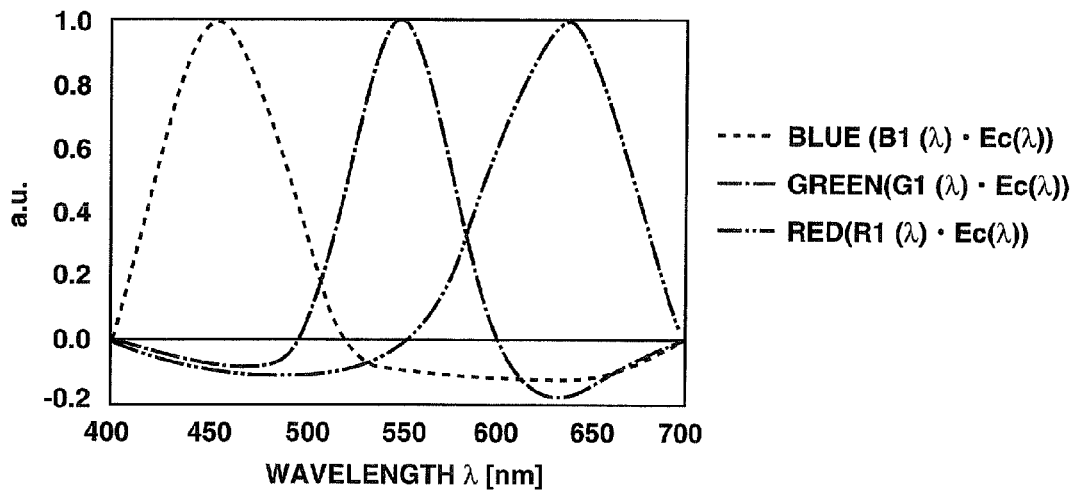
FIG. 5 is a view showing a spectral product of: spectral sensitivities (R1($\lambda$), G1($\lambda$), B1($\lambda$)) of RGB signals of a first CCD; and a comprehensive spectral product Ec($\lambda$) in a system from a light source to an objective optical system of an endoscope in a conventional synchronous type endoscope system.
Figure 6:
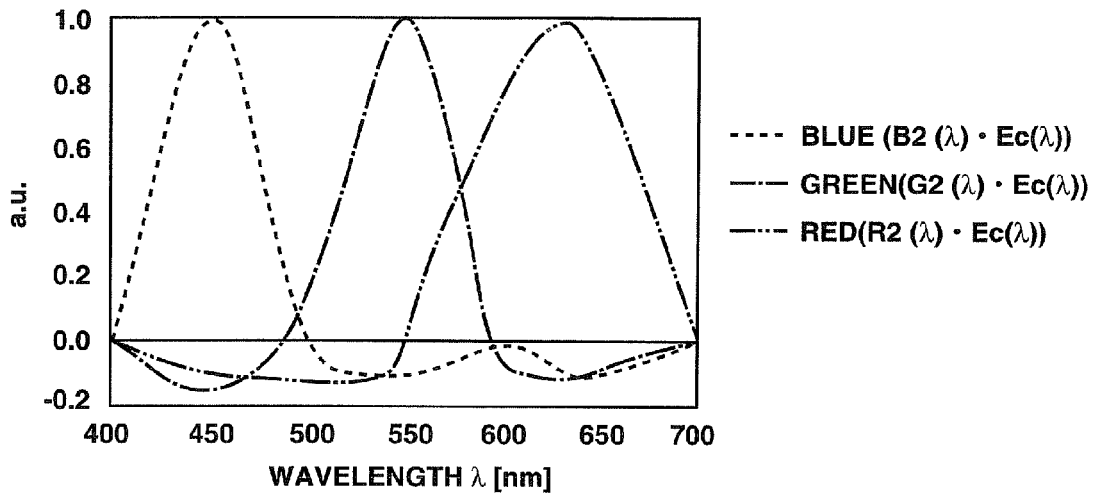
FIG. 6 is a view showing a spectral product of: spectral sensitivities (R2($\lambda$), G2($\lambda$), B2($\lambda$)) of RGB signals of a second CCD; and a comprehensive spectral product Ec($\lambda$) in the system from the light source to the objective optical system of the endoscope in the conventional synchronous type endoscope system.
Figure 7:
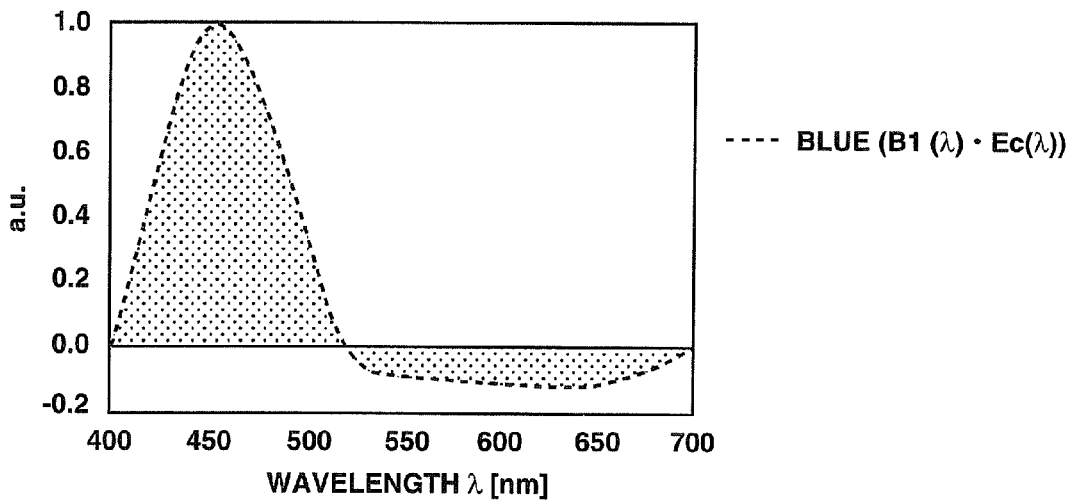
FIG. 7 is a view showing the spectral product of the B signal in FIG. 5.
Figure 8:
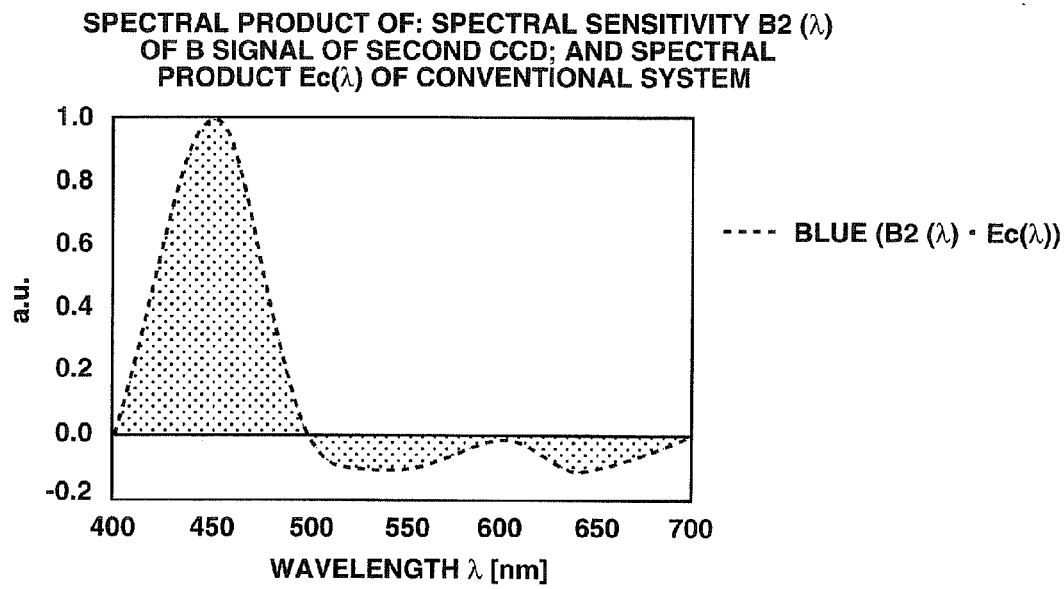
FIG. 8 is a view showing the spectral product of the B signal in FIG. 6.
Figure 9:
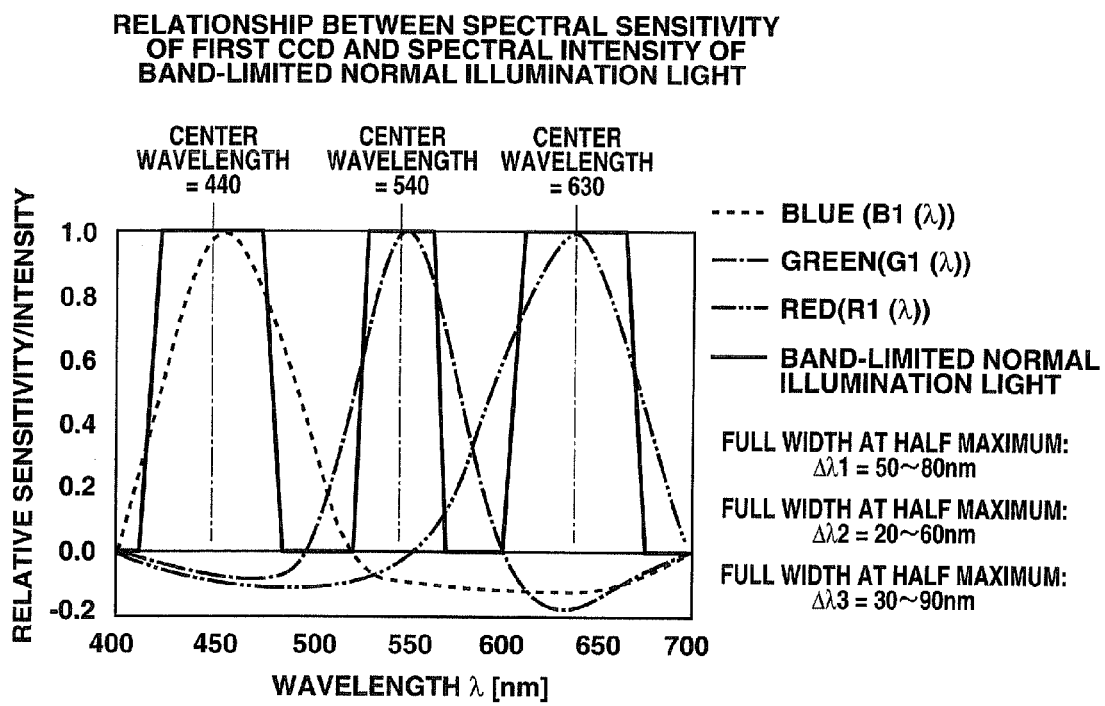
FIG. 9 is a view showing a relationship between the spectral sensitivities (R1($\lambda$), G1($\lambda$), B1($\lambda$)) of RGB signals of first CCD and spectral intensity characteristic of the band-limited normal illumination light that is exhibited by the band-limiting filter in FIG. 2.
Figure 10:
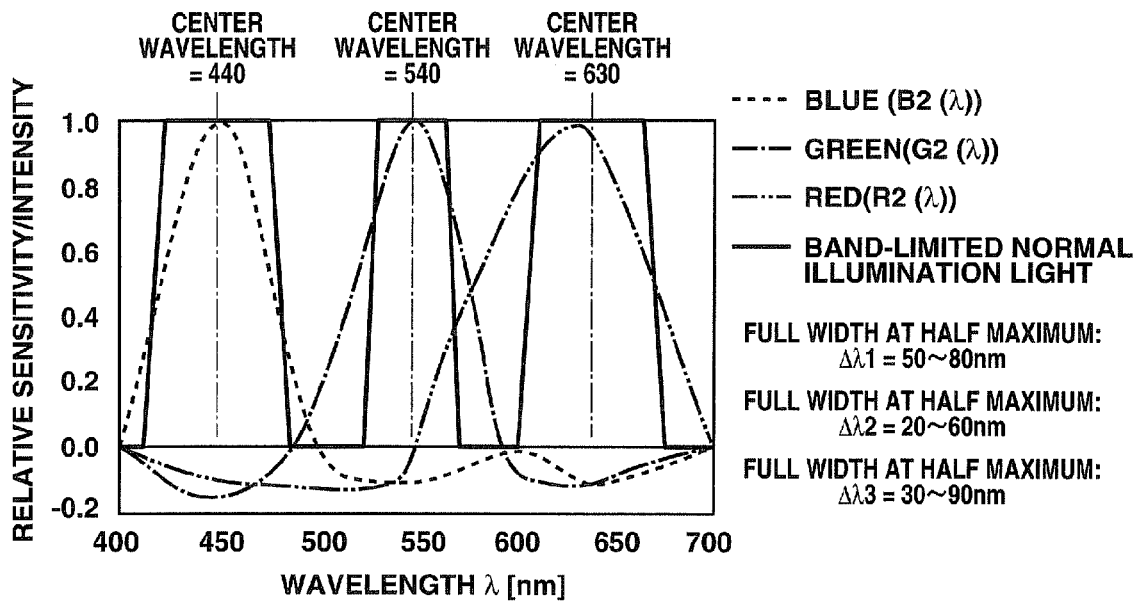
FIG. 10 is a view showing a relationship between the spectral sensitivities (R2 ($\lambda$), G2($\lambda$), B2($\lambda$)) of RGB signals of the second CCD and the spectral intensity characteristic of the band-limited normal illumination light that is exhibited by the band-limiting filter in FIG. 2.
Figure 11:
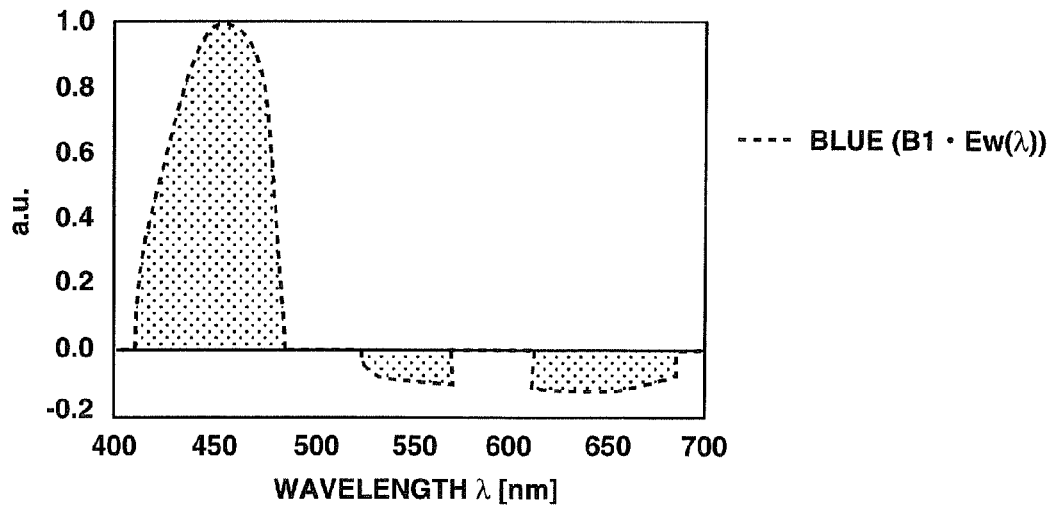
FIG. 11 is a view showing the spectral product of: the spectral sensitivity (B1($\lambda$)) of the B signal of the first CCD; and the comprehensive spectral product Ew($\lambda$) in the system from the light source to the objective optical system of the endoscope, the comprehensive spectral product including the spectral transmission characteristic of the band-limiting filter.
Figure 12:
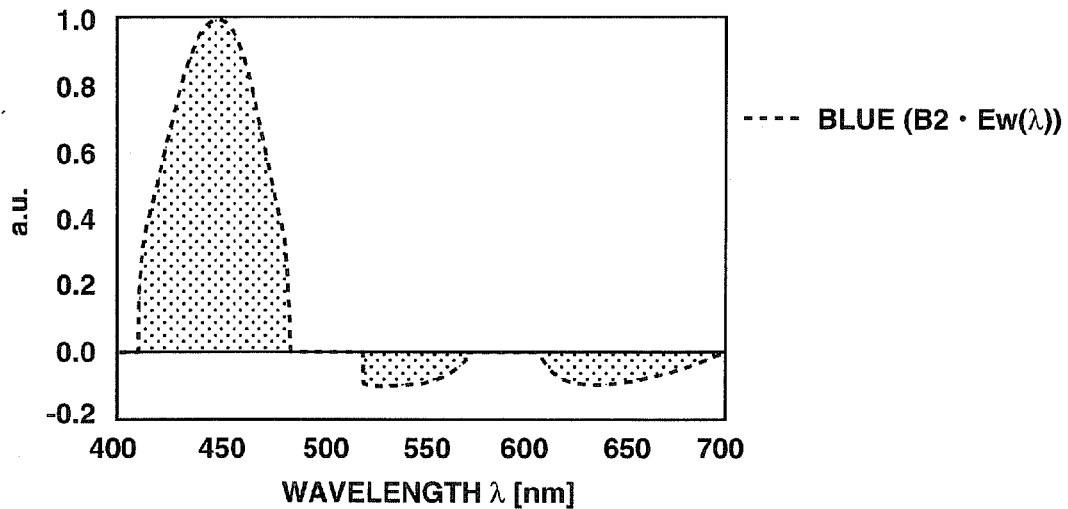
FIG. 12 is a view showing the spectral product of: the spectral sensitivity (B2($\lambda$)) of the B signal of the second CCD; and the comprehensive spectral product Ew($\lambda$) in the system from the light source to the objective optical system of the endoscope, the comprehensive spectral product including the spectral transmission characteristic of the band-limiting filter.
Figure 13:
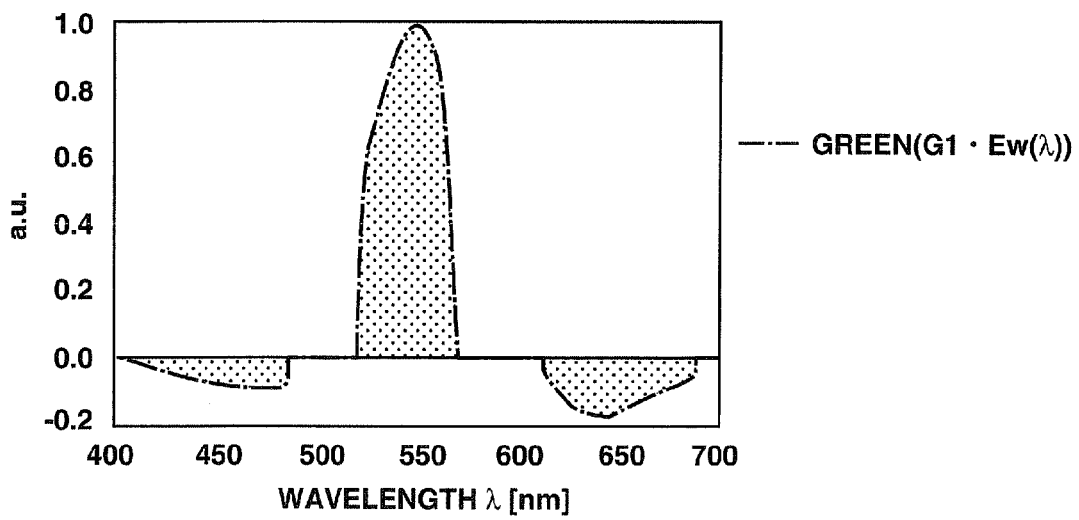
FIG. 13 is a view showing the spectral product of: the spectral sensitivity (G1($\lambda$)) of the G signal of the first CCD; and the comprehensive spectral product Ew($\lambda$) in the system from the light source to the objective optical system of the endoscope, the comprehensive spectral product including the spectral transmission characteristic of the band-limiting filter.
Figure 14:
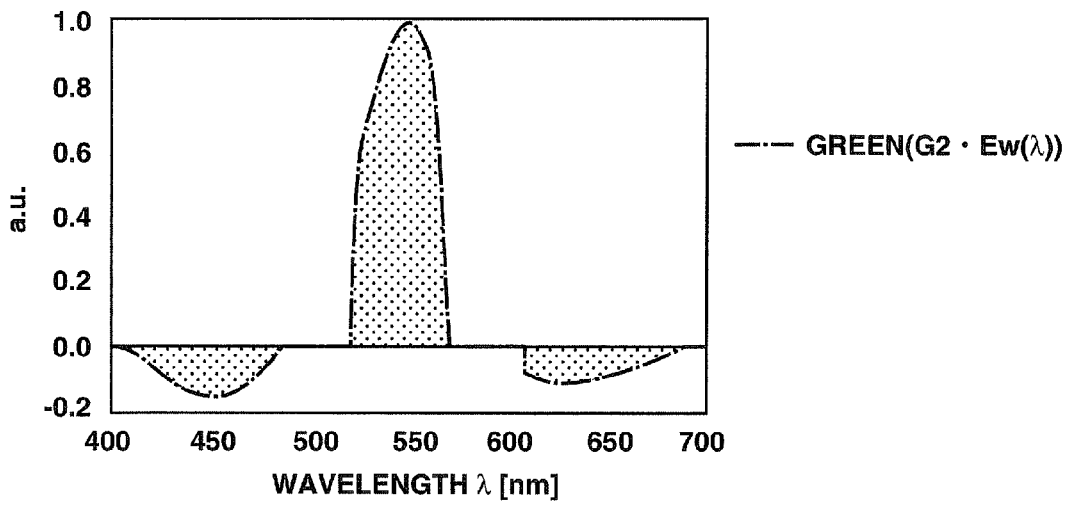
FIG. 14 is a view showing the spectral product of: the spectral sensitivity (G2($\lambda$)) of the G signal of the second CCD; and the comprehensive spectral product Ew($\lambda$) in the system from the light source to the objective optical system of the endoscope, the comprehensive spectral product including the spectral transmission characteristic of the band-limiting filter.
Figure 15:
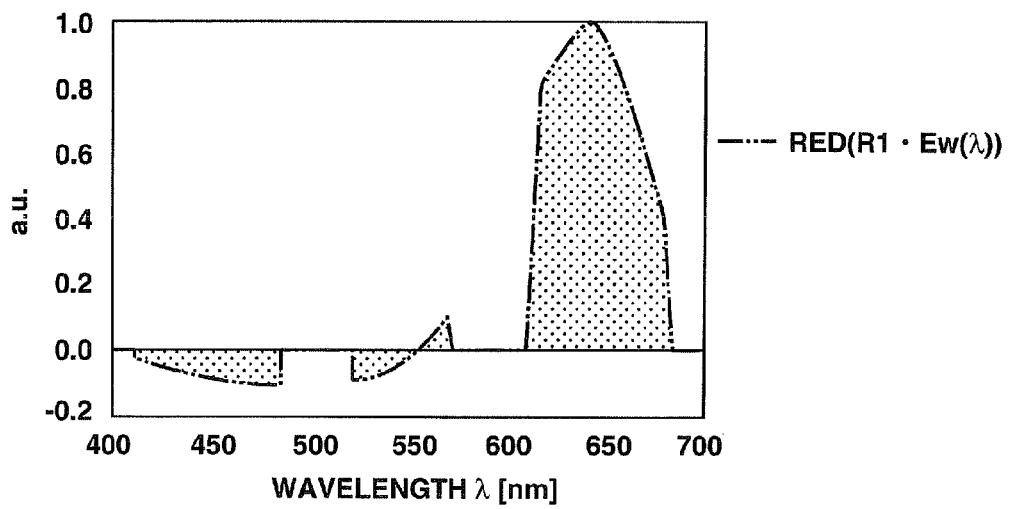
FIG. 15 is a view showing a spectral product of: the spectral sensitivity (R1($\lambda$)) of the R signal of the first CCD; and the comprehensive spectral product Ew($\lambda$) in the system from the light source to the objective optical system of the endoscope, the comprehensive spectral product including the spectral transmission characteristic of the band-limiting filter.
Figure 16:
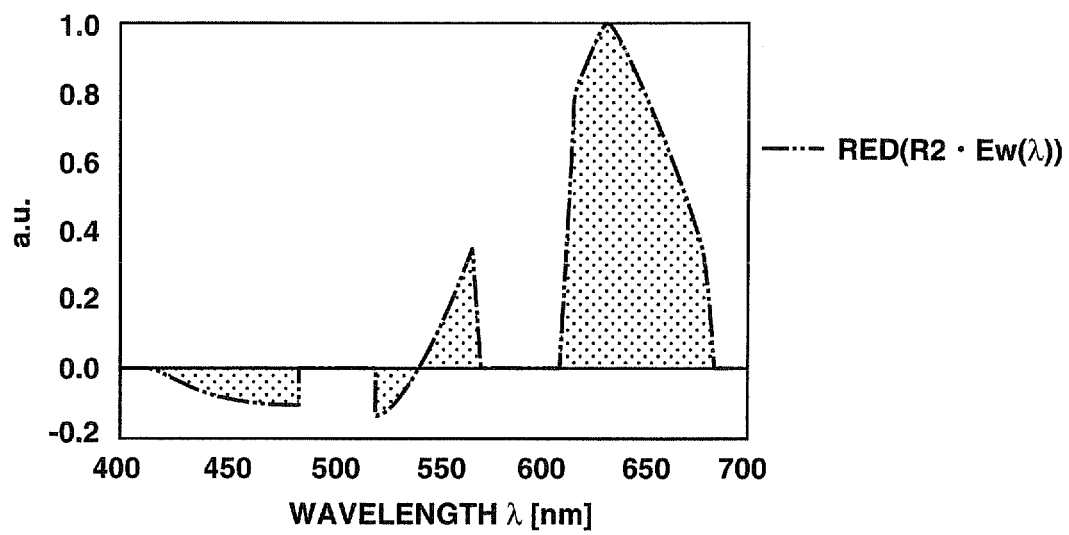
FIG. 16 is a view showing the spectral product of: the spectral sensitivity (R2 ($\lambda$)) of the R signal of the second CCD; and the comprehensive spectral product Ew($\lambda$) in the system from the light source to the objective optical system of the endoscope, the comprehensive spectral product including the spectral transmission characteristic of the band-limiting filter.
Figure 17:
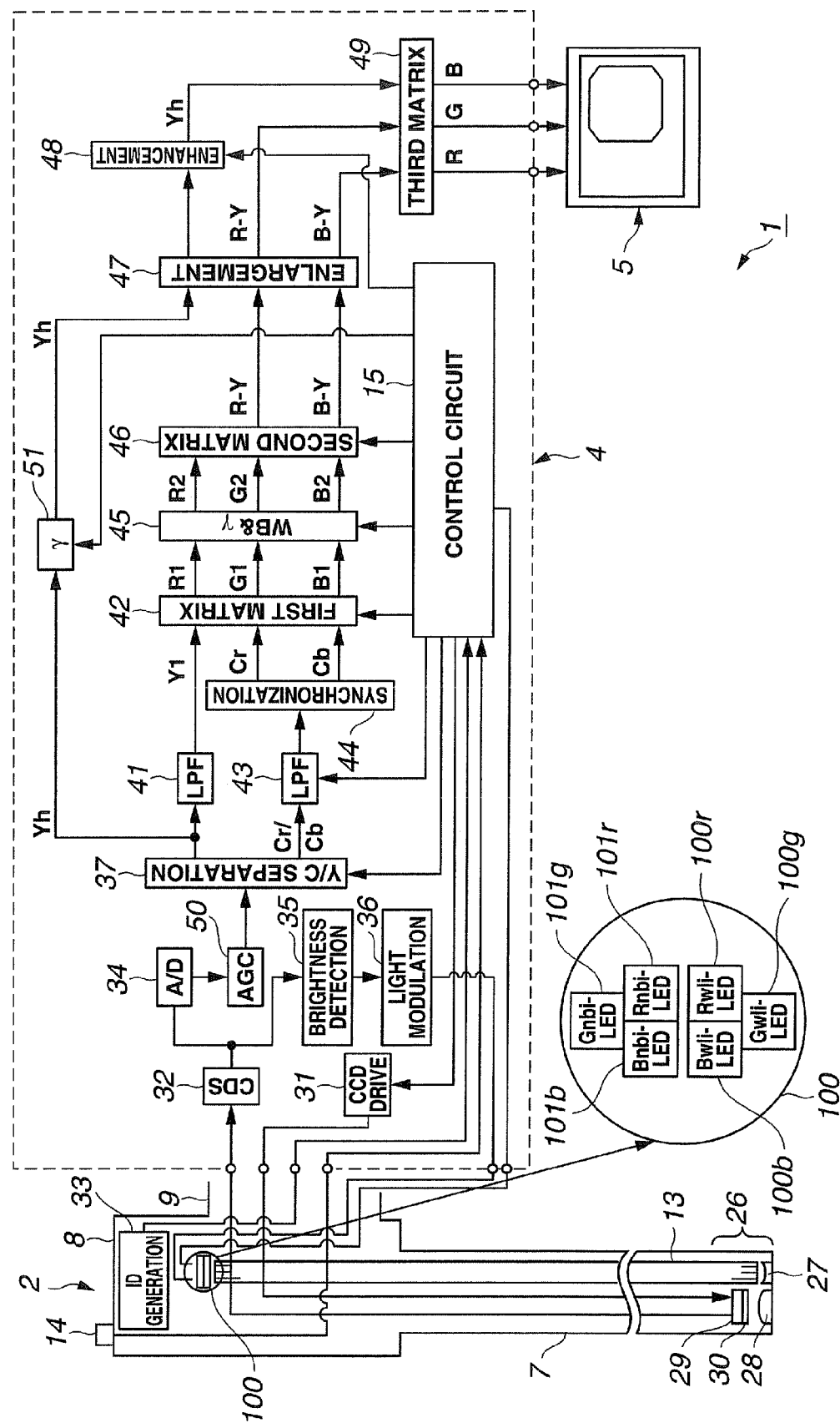
FIG. 17 is a view showing a modified example of the endoscope apparatus in FIG. 1.

FIGS. 1 to 17 relate to the embodiment 1 of the present invention. FIG. 1 is a configuration diagram showing a configuration of an endoscope apparatus. FIG. 2 is a view showing a configuration of a filter in FIG. 1. FIG. 3 is a view showing one example of spectral characteristics of RGB lights exhibited by a narrow-band filter in FIG. 2. FIG. 4 is a view showing one example of spectral characteristics of RGB lights exhibited by a band-limiting filter in FIG. 2. FIG. 5 is a view showing a spectral product of: spectral sensitivities (R1 ($\lambda$), G1($\lambda$), B1($\lambda$)) of RGB signals of a first CCD; and a comprehensive spectral product Ec($\lambda$) in a system from a light source to an objective optical system of an endoscope in a conventional synchronous type endoscope system. FIG. 6 is a view showing a spectral product of: spectral sensitivities (R2($\lambda$), G2($\lambda$), B2($\lambda$)) of RGB signals of a second CCD; and a comprehensive spectral product Ec($\lambda$) in the system from the light source to the objective optical system of the endoscope in the conventional synchronous type endoscope system. FIG. 7 is a view showing the spectral product of the B signal in FIG. 5. FIG. 8 is a view showing the spectral product of the B signal in FIG. 6. FIG. 9 is a view showing a relationship between the spectral sensitivities (R1($\lambda$), G1($\lambda$), B1($\lambda$)) of RGB signals of the first CCD and spectral intensity characteristic of the band-limited normal illumination light that is exhibited by the band-limiting filter in FIG. 2. FIG. 10 is a view showing a relationship between the spectral sensitivities (R2 (λ), G2(λ), B2(λ)) of RGB signals of the second CCD and the spectral intensity characteristic of the band-limited normal illumination light that is exhibited by the band-limiting filter in FIG. 2. FIG. 11 is a view showing the spectral product of: the spectral sensitivity (B1(λ)) of the B signal of the first CCD; and the comprehensive spectral product Ew(λ) in the system from the light source to the objective optical system of the endoscope, the comprehensive spectral product including the spectral transmission characteristic of the band-limiting filter. FIG. 12 is a view showing the spectral product of: the spectral sensitivity (B2(λ)) of the B signal of the second CCD; and the comprehensive spectral product Ew(λ) in the system from the light source to the objective optical system of the endoscope, the comprehensive spectral product including the spectral transmission characteristic of the band-limiting filter. FIG. 13 is a view showing the spectral product of: the spectral sensitivity (G1(λ)) of the G signal of the first CCD; and the comprehensive spectral product Ew(λ) in the system from the light source to the objective optical system of the endoscope, the comprehensive spectral product including the spectral transmission characteristic of the band-limiting filter. FIG. 14 is a view showing the spectral product of: the spectral sensitivity (G2(λ)) of the G signal of the second CCD; and the comprehensive spectral product Ew(λ) in the system from the light source to the objective optical system of the endoscope, the comprehensive spectral product including the spectral transmission characteristic of the band-limiting filter. FIG. 15 is a view showing a spectral product of: the spectral sensitivity (R1(λ)) of the R signal of the first CCD; and the comprehensive spectral product Ew(λ) in the system from the light source to the objective optical system of the endoscope, the comprehensive spectral product including the spectral transmission characteristic of the band-limiting filter. FIG. 16 is a view showing the spectral product of: the spectral sensitivity (R2(λ)) of the R signal of the second CCD; and the comprehensive spectral product Ew(λ) in the system from the light source to the objective optical system of the endoscope, the comprehensive spectral product including the spectral transmission characteristic of the band-limiting filter. FIG. 17 is a view showing a modified example of the endoscope apparatus in FIG. 1.

As shown in FIG. 1, an endoscope apparatus 1 according to the embodiment 1 includes: an electronic endoscope (hereinafter shortened as endoscope) 2 which is inserted into a body cavity and the like for endoscopic inspections; a light source device 3 for supplying illumination light to the endoscope 2; a video processor 4, as a video signal processing device for endoscope, for driving image pickup means incorporated in the endoscope 2 and performing signal processing on an output signal from the image pickup means; and a monitor 5 for displaying an endoscopic image picked up by the image pickup means in response to input of a video signal outputted from the video processor 4.

The endoscope 2 includes an elongated insertion portion 7, an operation portion 8 provided at a rear end of the insertion portion 7, and a universal cable 9 extended from the operation portion 8. A light guide connector 11 at an end portion of the universal cable 9 is detachably connected to the light source device 3, and a signal connector is detachably connected to the video processor 4.

A light guide 13 for transmitting illumination light is inserted through the insertion portion 7. By connecting the light guide connector 11 located at an end portion on a hand side of the light guide 13 to the light source device 3, the illumination light from the light source device 3 is supplied to the light guide 13.

In a normal light observation mode, the light source device 3 generates band-limited normal illumination light (WLI) of RGB lights by limiting the illumination light in a visible region of RGB as normal illumination light to within a predetermined bandwidth suitable for normal observation, and supplies the generated illumination light to the light guide 13. In addition, in a narrow-band light observation mode, the light source device 3 generates narrow-band illumination light (NBI) as illumination light in narrow band suitable for narrow-band observation, to supply the generated narrow-band illumination light to the light guide 13.

Instruction to switch between the normal light observation mode and narrow-band light observation mode can be performed using a mode-switching switch 14 configured of a scope switch and the like which are provided to the operation portion 8 of the endoscope 2, for example. Note that the mode-switching switch 14 may be configured of a foot switch instead of the scope switch provided to the endoscope 2, or alternatively may be provided on a front panel of the video processor 4, or configured of a keyboard not shown.

A switch signal outputted from the mode-switching switch 14 is inputted to a control circuit 15 in the video processor 4. When the switching signal is inputted, the control circuit 15 controls a filter switching mechanism 16 of the light source device 3 to selectively switch the band-limited normal illumination light and narrow-band illumination light.

In addition, the control circuit 15 also performs control to switch the characteristics of the video signal processing system in the video processor 4 in conjunction with the switching control of the illumination light to be supplied from the light source device 3 to the light guide 13. In response to the switching operation with the mode-switching switch 14, the control circuit 15 switches the characteristics of the video signal processing system, thereby performing signal processing suitable for each of the normal light observation mode and the narrow-band light observation mode.

The light source device 3 incorporates a lamp 20 for generating illumination light. The lamp 20 generates illumination light including a visible light region. Infrared light of the illumination light is cut by an infrared cut filter 21, and the resultant light is then incident on a diaphragm 22. The diaphragm 22 has its opening amount adjusted by a diaphragm drive circuit 23, and thereby the light amount passing therethrough is controlled.

The illumination light which has passed through the diaphragm 22 is incident on a condensing lens 25 via a filter 24 in an illumination light path by the filter switching mechanism 16, either by passing through a narrow-band filter 24a of the filter 24 (in the narrow-band light observation mode), or by passing through a band-limiting filter 24b as band-limited normal illumination light generation means of the filter 24 (in the normal light observation mode), as shown in FIG. 2. The illumination light is then condensed by the condensing lens 25 and incident onto the end face of the hand side of the light guide 13, that is, the incident end face thereof.

FIG. 3 shows one example of spectral characteristics of RGB lights exhibited by the narrow-band filter 24a. The narrow-band filter 24a exhibits a trimodal filter characteristic, and, for example, includes a narrow-band transmittance filter characteristic portions Ra, Ga, and Ba for the respective wavelength regions of red, green and blue.

More specifically, the narrow-band transmittance filter characteristic portions Ra, Ga, and Ba, for example, have bandpass characteristics in which the respective center wavelengths are 630 nm, 540 nm and 420 nm, respectively, and the full widths at half maximum λ0 are between 20 and 40 nm.

Therefore, when the narrow-band filter 24a is arranged in the illumination light path, a three-band narrow-band illumination light that transmits the narrow-band transmittance filter characteristic portions Ra, Ga, and Ba is incident onto the light guide 13.

FIG. 4 shows one example of spectral characteristics of RGB lights exhibited by the band-limiting filter 24b. The band-limiting filter 24b exhibits a trimodal filter characteristic, and, for example, includes a band-limiting transmittance filter characteristic portions Rb, Gb, and Bb for the wavelength regions of red, green and blue, respectively.

More specifically, the band-limiting transmittance filter characteristic portions Rb, Gb, and Bb, for example, have bandpass characteristics in which the respective center wavelengths are 630 nm (full width at half maximum $\lambda1$=30 to 90 nm), 540 nm (full width at half maximum $\lambda2$=20 to 60 nm), and 440 nm (full width at half maximum $\lambda3$=50 to 80 nm).

Therefore, when the band-limiting filter 24b is arranged in the illumination light path, a three-band band-limited normal illumination light that transmits the band-limiting transmittance filter characteristic portions Rb, Gb, and Bb is incident onto the light guide 13.

The illumination light to be emitted from the light guide 13 is transmitted by the light guide 13 onto a distal end surface thereof and emitted outside through an illumination lens 27 mounted to an illumination window provided to a distal end portion 26 of the insertion portion 7, to illuminate a surface of a living tissue such as diseased part in a body cavity.

The distal end portion 26 includes an observation window provided adjacently to the illumination window. To the observation window is mounted an objective lens 28. The objective lens 28 forms an optical image produced by reflected light from a living tissue. At the image-forming position of the objective lens 28 is arranged, as a solid-state image pickup device, a charge coupled device (abbreviated as CCD) 29 with which the optical image is photoelectrically converted.

Figure 18:
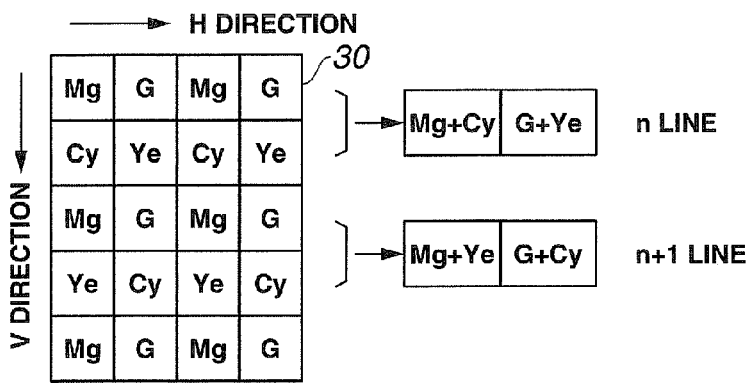
FIG. 18 is a view showing a configuration of a conventional complementary color filter.

On the image pickup surface of the CCD 29 is mounted, for example, a complementary color filter (see FIG. 18) on a pixel basis, as a color separation filter 30 for optically separating colors.

The complementary color filter has color chips in four colors, magenta (Mg), green (G), cyan (Cy) and yellow (Ye) which are arranged in front of the respective pixels with Mg and G being alternately arranged in the horizontal direction, and the arrays Mg, Cy, Mg, Ye and G, Ye, G, Cy being arranged in that order in the vertical direction.

In the CCD 29 using the complementary color filter, the video processor 4 adds two columns of pixels adjacent to each other in the vertical direction and sequentially reads out the pixels such that the columns of pixels are shifted with respect to each other in odd fields and even fields. A luminance signal and color difference signals are then generated, as is known, by the color separation circuit in the subsequent stage.

The CCD 29 is connected to one end of a signal line, and the other end of the signal line is connected to a signal connector. By connecting this signal connector to the video processor 4, the CCD 29 is connected to a CCD drive circuit 31 and a CDS circuit 32 in the video processor 4.

Each endoscope 2 includes an ID generation section 33 which generates identification information (ID) unique to the endoscope 2. The ID generated by the ID generation section 33 is inputted to the control circuit 15. The control circuit 15 uses the ID to identify the type of endoscope 2 connected to the video processor 4, and the number of pixels, the type, and the like of the CCD 29 incorporated into the endoscope 2.

The control circuit 15 then controls the CCD drive circuit 31 to appropriately drive the CCD 29 of the identified endoscope 2.

In response to the application of a CCD drive signal from the CCD drive circuit 31, the CCD 29 inputs an image pickup signal, which is subjected to photoelectric conversion, to a correlated double sampling circuit (abbreviated CDS circuit) 32. After signal components have been extracted from the image pickup signal and converted into a baseband signal by the CDS circuit 32, the baseband signal is inputted to an A/D conversion circuit 34, converted into a digital signal, and inputted to a brightness detection circuit 35, and thereafter brightness (the average luminance of a signal) is detected.

A brightness signal detected by the brightness detection circuit 35 is inputted to a light modulation circuit 36, and a light modulation signal is generated for carrying out light modulation in accordance with the difference with reference brightness (target value of modulated light). The light modulation signal from the light modulation circuit 36 is inputted to the diaphragm drive circuit 23, and the opening amount of the diaphragm 22 is adjusted so as to achieve the reference brightness.

The digital signal outputted from the A/D conversion circuit 34 is gain-controlled by an auto-gain controller (abbreviated as AGC) 50, and thereafter inputted to a Y/C separation circuit 37, and a luminance signal Y and line-sequential color difference signals Cr (=2R−G) and Cb (=2B−G) (as broadly defined color signals C) are generated. Note that the AGC 50 controls the gain such that signal level becomes a predetermined level by compensating the decrease in the signal level caused when light amount at the time of normal observation is insufficient due to the band limitation by the band-limiting filter 24b.

The luminance signal Y is inputted to a selector 39 (this luminance signal is referred to as Yh) and also inputted to a first low-pass filter (abbreviated as LPF) 41 for limiting the pass band of the signal.

The LPF 41 is set to have a broad pass band in accordance with the luminance signal Y. The luminance signal Y1 in the band set by the pass-band characteristic of the LPF 41 is inputted to a first matrix circuit 42.

In addition, the color difference signals Cr and Cb are inputted to a synchronization circuit 44 through a second LPF 43 for limiting the pass bands of the signals.

In this case, the pass-band characteristic of the second LPF 43 is changed by the control circuit 15 according to the observation modes. Specifically, in the normal light observation mode, the second LPF 43 is set to have a lower pass band than the first LPF 49.

On the other hand, in the narrow-band light observation mode, the second LPF 43 is set to have broader pass band than the low band in the normal light observation mode. For example, the second LPF 43 is set (changed) to have a broad pass band almost similarly as the first LPF 41. The second LPF 43 thus forms processing characteristic changing means for changing processing characteristics to limit pass band for the color difference signals Cr, Cb in conjunction with the switching of the observation modes.

The synchronization circuit 44 synchronizes the color difference signals Cr, Cb alternately obtained for each line, and the synchronized color difference signals Cr, Cb are inputted to the first matrix circuit 42.

The first matrix circuit 42 converts the luminance signal Y and color difference signals Cr, Cb into three primary color signals R, G, and B, and outputs the converted signals to a white balance & γ-correction circuit (abbreviated as WB & γ) 45.

Furthermore, the first matrix circuit 42 is controlled by the control circuit 15, to change the value of matrix coefficients (which determine the conversion characteristics) according to the characteristics of the narrow-band filter 24a and the band-limiting filter 24b, and converts the signals R, G, and B into the color signals R1, G1, and B1 having no or almost no color mixture.

Signals R2, G2, B2 subjected to white balance processing and γ-correction processing in the WB & γ 45 are inputted to the second matrix circuit 46 to be converted into the luminance signal Y and color difference signals R-Y, B-Y.

In this case, in the normal light observation mode, the control circuit 15 sets the matrix coefficients of the second matrix circuit 46 so as to simply convert the signals R2, G2, and B2 into a luminance signal Y and color difference signals R-Y, B-Y.

In the narrow-band light observation mode, the control circuit 15 changes the matrix coefficients of the second matrix circuit 46 from the value in the normal light observation mode, setting this value such that the color difference signals R-Y, B-Y based on the luminance signal Y in which the ratio (weighting) for the B signal is increased in particular are generated from the signals R2, G2, B2. That is, the color difference signals R-Y, B-Y obtained using the expression below are generated.

[Expression 2]

$$\begin{pmatrix} Y \\ R-Y \\ B-Y \end{pmatrix} = M2 \begin{pmatrix} R2 \\ G2 \\ B2 \end{pmatrix} \quad (2)$$

$$M2 = M3^{-1} M2'$$

$$WLI: M2' = I$$

$$NBI: M2' = K = \begin{pmatrix} 0 & m12 & 0 \\ 0 & 0 & m23 \\ 0 & 0 & m33 \end{pmatrix}$$

Here, M2 is a matrix (three rows and three columns) of the second matrix circuit 46, $M3^{-1}$ is inverse matrix (three rows and three columns) of the matrix M3 applied in a third matrix circuit 49, the matrix M2' is the matrix I in the normal observation mode and is the matrix K in the narrow-band observation mode. I represents an identity matrix (three rows and three columns), and m12, m23, and m33 are real numbers.

The color difference signals R-Y and B-Y outputted from the second matrix circuit 46 are inputted to an enlargement circuit 47, together with the luminance signal Yh which is outputted from the Y/C separation circuit 37 and then passes through the γ-correction circuit 51.

The luminance signal Yh subjected to enlargement processing by the enlargement circuit 47 is contour-enhanced by an enhancement circuit 48, and thereafter inputted to the third matrix circuit 49. The color difference signals R-Y, B-Y subjected to enlargement processing by the enlargement circuit 47 are inputted to the third matrix circuit 49.

The γ-correction circuit 51 is controlled by the control circuit 15 and operates together with the Wb & γ 45 to perform γ-correction. Specifically, in the narrow-band light observation mode, the γ-correction characteristic is changed such that the correction value with respect to low luminance is smaller and the correction value with respect to high luminance is larger than in the normal light observation mode. Thus the contrast is enhanced, which makes the display characteristic easier to identify.

The color difference signals R-Y, B-Y which have passed through the enlargement circuit 47 are inputted to the third matrix circuit 49 without passing through the enhancement circuit 48.

The color difference signals R-Y, B-Y are then converted into RGB signals by the third matrix circuit 49, and thereafter converted into an analog video signal by a D/A conversion circuit, not shown, to be outputted from a video signal output terminal to the monitor 5.

Figure 19:
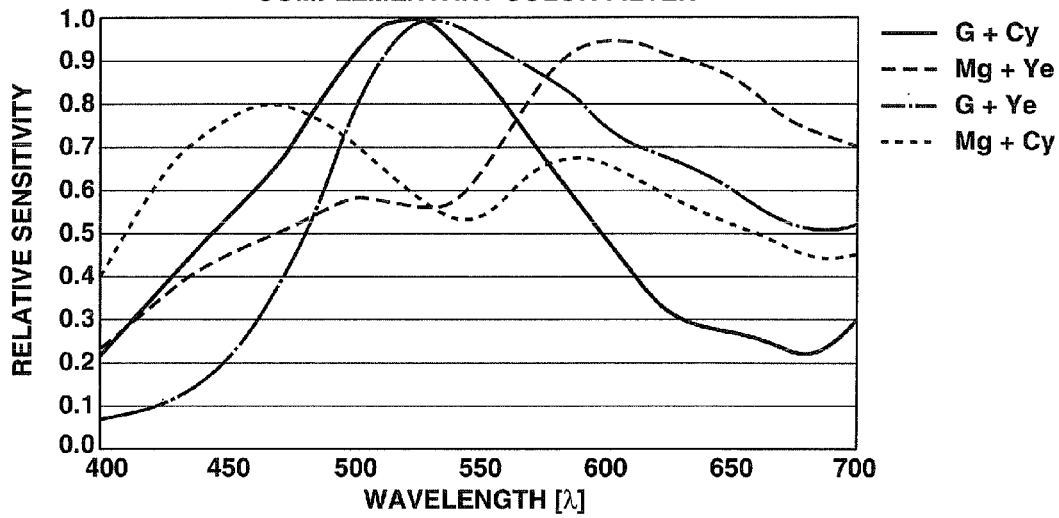
FIG. 19 is a first view showing spectral characteristics of readout signals of the complementary color filter in FIG. 18.
Figure 20:
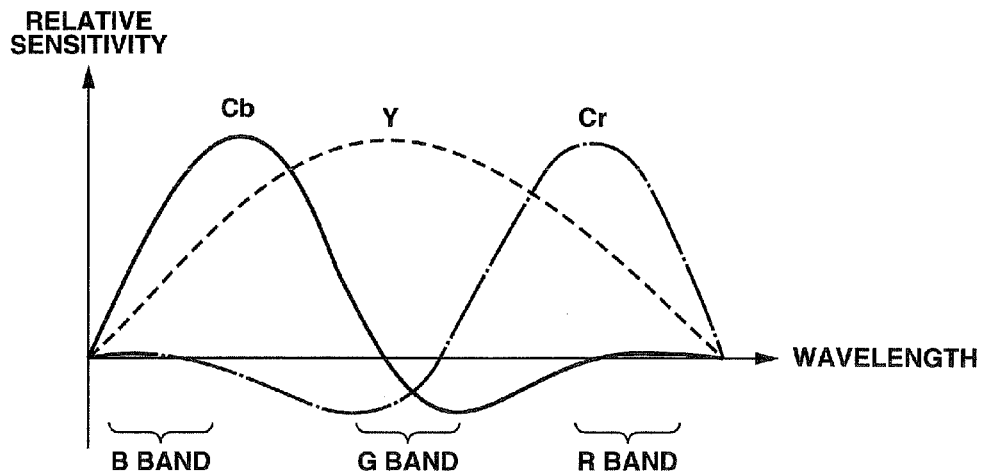
FIG. 20 is a view showing spectral characteristics of a luminance signal and color difference signals based on the readout signals in FIG. 19.
Figure 21:
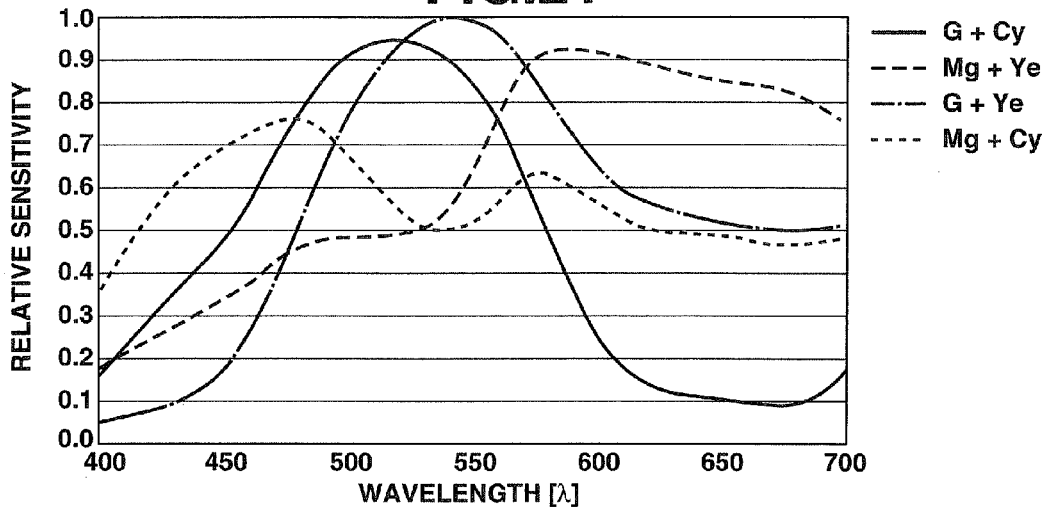
FIG. 21 is a second view showing the spectral characteristics of the readout signals of the complementary color filter in FIG. 18.
Figure 23:
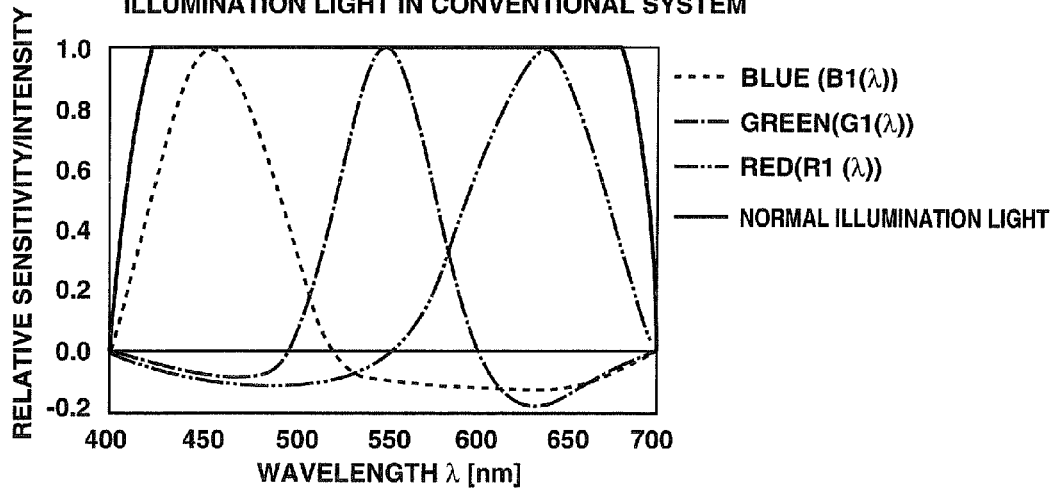
FIG. 23 is a view showing a relationship between the spectral sensitivities (R1($\lambda$), G1($\lambda$), B1($\lambda$)) of the RGB signals of the first CCD and the spectral intensity characteristic of the normal illumination light emitted from the distal end of the endoscope in the conventional synchronous type endoscope system.
Figure 24:
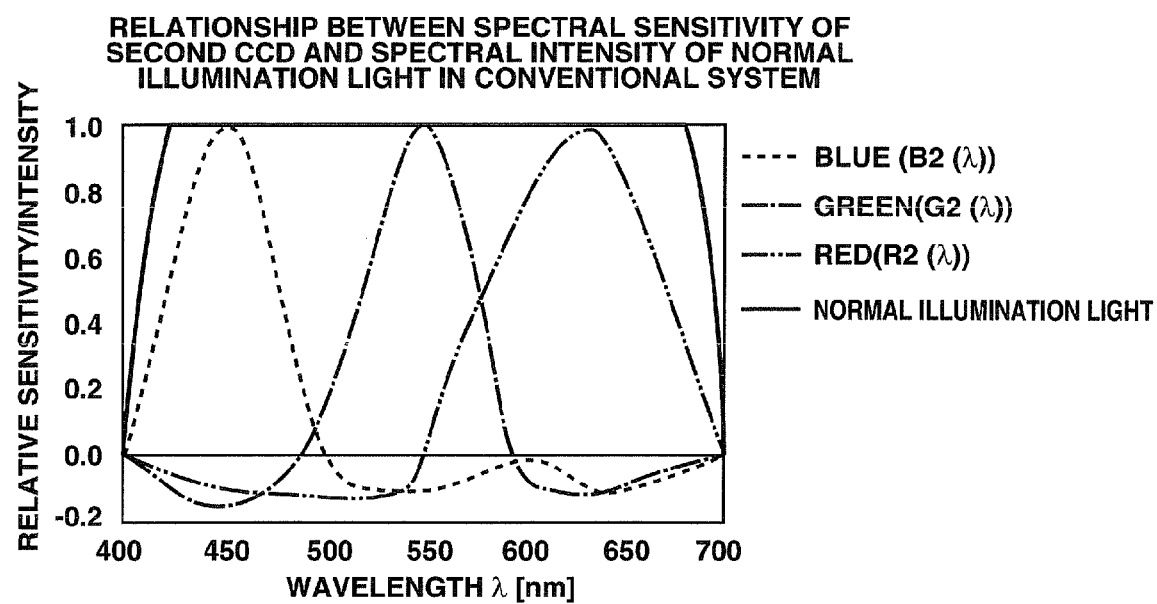
FIG. 24 is a view showing a relationship between the spectral sensitivities (R2($\lambda$), G2($\lambda$), B2($\lambda$)) of the RGB signals of the second CCD and the spectral intensity characteristic of the normal illumination light emitted from the distal end of the endoscope in the conventional synchronous type endoscope system.

Since the spectral characteristics of the complementary color filters are different from one CCD to another as shown in FIGS. 19, 21, the RGB signals have different spectral characteristics as shown in FIGS. 23, 24.

Figure 22:
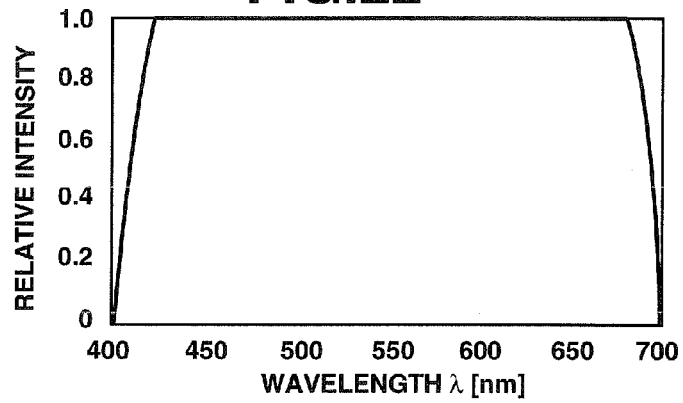
FIG. 22 is a view showing a spectral characteristic of normal illumination light emitted from a distal end of an endoscope in the conventional synchronous type endoscope system.

In a conventional synchronous type endoscope system, normal illumination light having the spectral intensity characteristic shown in FIG. 22 is irradiated. Therefore, as is understood from the relationship between the spectral sensitivity characteristic of the CCD and the spectral intensity characteristic of normal illumination light (see FIGS. 23, 24), the spectral distribution of the spectral product (E(λ)·Sx(λ) in the expression 1) of the spectral sensitivity characteristic of the CCD and the comprehensive spectral product Ec(λ) in the system from the light source to the objective optical system of the endoscope is almost the same as the distribution of the spectral sensitivity of the CCD, as shown in FIGS. 5 and 6. Note that the vertical axes in FIG. 5 and the like show arbitrary unit (a.u.=arbitrary unit).

Therefore, the spectral distributions of the spectral products remain greatly different from each other in the first and second CCDs, so that the intensity of the RGB signals, which is obtained by integrating the spectral product of the above-described spectral product and the spectral reflectance of the subject, is different for each of the CCDs.

Making description by taking the B signal as an example, even if the subject is the same living mucosa, the characteristic of the spectral product of the spectral sensitivity of the B signal of the CCD is different in the first CCD and the second CCD, and as a result, the intensity of the B signal is different for each of the CCDs, as shown in FIGS. 7 and 8.

To the contrary, in the present embodiment, as is understood from the relationship between the spectral sensitivity characteristics of the CCDs and the spectral intensity characteristic of the band-limited normal illumination light as shown in FIGS. 9, 10, change in the spectral distribution of the spectral product of the spectral sensitivity characteristics of RGB signals of the CCD and the comprehensive spectral product Ew (λ), which includes a spectral transmission factor characteristic of the band-limiting filter 24b, in the system from the light source to the objective optical system of the endoscope remains within the band limited by the band-limiting filter 24b, if description is made by taking the B signal as an example, as shown in FIGS. 11, 12. Accordingly, the difference of spectral sensitivities of the CCDs can be restrained. Therefore, integral values of the spectral product of the spectral sensitivity and the spectral product Ew (λ) are almost the same in the first and second CCDs. As a result, the intensity of the B signal can be almost the same for each of the CCDs.

Note that, also as for the G and R signals, the change in the spectral distribution remains within the band limited by the band-limiting filter 24b as shown in FIGS. 13 to 16. Therefore, the difference of the spectral sensitivities of the CCDs can be similarly restrained.

Thus, in the present embodiment, the illumination light to be irradiated is limited within the band of common spectral component of the spectral characteristic of the complementary color filter. Therefore, the integral values of the spectral products are substantially the same, and the image quality including the color tone and the like of a normal image to be obtained is not affected by the spectral characteristic of each of the CCDs. As a result, stable image quality can be maintained. Note that the present embodiment can be applied also to a CCD including a primary color filter.

Note that, in the present embodiment, the light source device is provided, and the band-limited normal illumination light and the narrow-band illumination light are irradiated to the subject through the light guide 13 by switching the filter 24 in the light source device. However, there is no limitation placed thereon. For example, as shown in FIG. 17, the same working and effect as those in the present embodiment can be obtained also when an LED unit 100 is provided to the operation portion 8 to irradiate the subject with lights emitted from LEDs mounted to the LED unit 100 by introducing the lights to the illumination lens 27 by the common light guide 13 and pick up an image with the CCD 29, the LEDs being LEDs (Rwli-LED 100*r*, Gwli-LED 100G, and Bwli-LED 100B) as band-limited normal illumination light generation means for emitting band-limited normal illumination light and LEDs (Rnbi-LED 101*r*, Gnbi-LED 101*g*, and Bnbi-LED 101*b*) for emitting narrow-band illumination light.

The present invention is not limited to the above-described embodiment, and various changes and modifications are possible without departing from the scope of the present invention.

What is claimed is:

1. An endoscope apparatus for performing signal processing to generate a video signal based on a signal outputted from an image pickup section which is mounted to an endoscope and includes a color separation optical filter to perform color image pickup, the endoscope apparatus comprising:

a band-limited normal illumination light generation section for generating, by one filter, a discrete band-limited normal illumination light which concurrently includes only a light limited in visible light range of red to within a bandwidth with a predetermined light amount, a light limited in visible light range of green to within a bandwidth with a predetermined light amount, and a light limited in visible light range of blue to within a bandwidth with a predetermined light amount, in a normal-band light observation mode, the bandwidths of the light limited in visible light range of red, the light limited in visible light range of green and the light limited in visible light range of blue having no overlap in full widths at half maximum of relative intensities; and a narrow-band light generation section for generating at least one discrete narrow-band light whose bandwidth is narrower that the bandwidth limited by the band-limited normal illumination light generation section, in a narrow-band light observation mode.

2. The endoscope apparatus according to claim 1, wherein the color separation optical filter in the image pickup section is a complementary color filter.

3. The endoscope apparatus according to claim 1, further comprising a gain control section for controlling a gain of the signal outputted from the image pickup section under the discrete band-limited normal illumination light to a predetermined gain.

4. The endoscope apparatus according to claim 1, wherein the bandwidth limited by the band-limited normal illumination light generation section is defined by a spectral characteristic of the color separation optical filter.

5. The endoscope apparatus according to claim 1, wherein the band-limited normal illumination light generation section generates the band-limited normal illumination light which has wavelength bandwidths defined by a spectral characteristics of the color separation optical filter and is discrete within the visible light range.

6. The endoscope apparatus according to claim 1, wherein the light limited in visible light range of red to within the bandwidth with the predetermined light amount, the light limited in visible light range of green to within the bandwidth with the predetermined light amount and the light limited in visible light range of blue to within the bandwidth with the predetermined light amount are separated to have no overlap of relative intensities of the lights in all visible light range.

* * * * *